(12) United States Patent
Cash, Jr.

(10) Patent No.: US 6,195,410 B1
(45) Date of Patent: Feb. 27, 2001

(54) X-RAY INTERFEROMETER

(75) Inventor: Webster C. Cash, Jr., Boulder, CO (US)

(73) Assignee: Focused X-Rays, LLC, Boulder, CO (US)

( * ) Notice: Subject to any disclaimer, the term of this patent is extended or adjusted under 35 U.S.C. 154(b) by 0 days.

(21) Appl. No.: 09/491,956

(22) Filed: Jan. 26, 2000

Related U.S. Application Data

(60) Provisional application No. 60/117,302, filed on Jan. 26, 1999.

(51) Int. Cl.[7] .................................................. G01N 23/06
(52) U.S. Cl. ................................. 378/43; 378/36; 378/85; 356/353
(58) Field of Search ................................. 378/36, 43, 85, 378/84; 356/354, 353

(56) References Cited

U.S. PATENT DOCUMENTS

| | | | |
|---|---|---|---|
| 4,912,737 | * | 3/1990 | Ohsuka et al. ........................ 378/43 |
| 4,941,163 | * | 7/1990 | Hoover .................................. 378/43 |
| 5,604,782 | * | 2/1997 | Cash, Jr. ............................... 378/85 |
| 5,881,126 | * | 3/1999 | Momose ................................ 378/36 |

OTHER PUBLICATIONS

Gunnar Kellstrom, Experimentelle Untersuchungen Uber Interferenz–Und Beugungserscheinungen Bei Langwelligen Rontgenstrahlen, Book, May 1932, Ser. IV, vol. 8, No. 5.

U. Bonse and M. Hart, an X–Ray Interferometer, Applied Physics Letter, Apr. 15, 1965, pp. 155–156, vol. 6 No. 8 Ithaca, New York, USA.

Howells, Frank, Hussain, Moler, Reich, Moller, and ShirleyToward a Soft X–Ray Fourier–transform Spectrometer, Nuclear Instruments & Methods in PhysicsResearch, 1994, pp. 182–191, Berkeley, CA, USA.

Polack, Joyeux, Svatos, and Phalippou, Applications of Wavefront Division Interferometers in Soft X Rays 1995 American Intsitute of Physics, Jul. 21, 1994, pp. 2180–2183, USA.

Baldwin et al., The First Images from an Optical Aperture Syntheses Array: Mapping of Capella with COAST at Two Epochs, Astronomy and Astrophysics, 1996, pp. L13–L16.

Van Speybroeck et al., Performance Expectation Versus Reality, SPIE, 1997, pp. 89–104, vol. 3113.

Gallagher et al., Sub–Arcsec X–Ray Telescope for Imaging the Solar Corona in the 0.25–1.2 keV Band, pp. 1–12, Boulder, CO, USA.

* cited by examiner

Primary Examiner—David V. Bruce
Assistant Examiner—Drew A. Dunn
(74) Attorney, Agent, or Firm—Dorr, Carson, Sloan & Birney, P.C.

(57) ABSTRACT

An interferometer that uses plane mirrors at grazing incidence to create interference fringes in the extreme ultraviolet and x-ray portions of the spectrum. X-ray interferometry has historically been implemented through narrow band, diffractive systems that split the wavefront. By using two separate optical channels at grazing incidence to create interference from two areas of the wavefront, this system has broad band response and much higher efficiency. The interferometer has applications to telescopes, microscopes and spectrometers in the extreme ultraviolet and x-ray, and high contrast imaging in the visible.

18 Claims, 10 Drawing Sheets

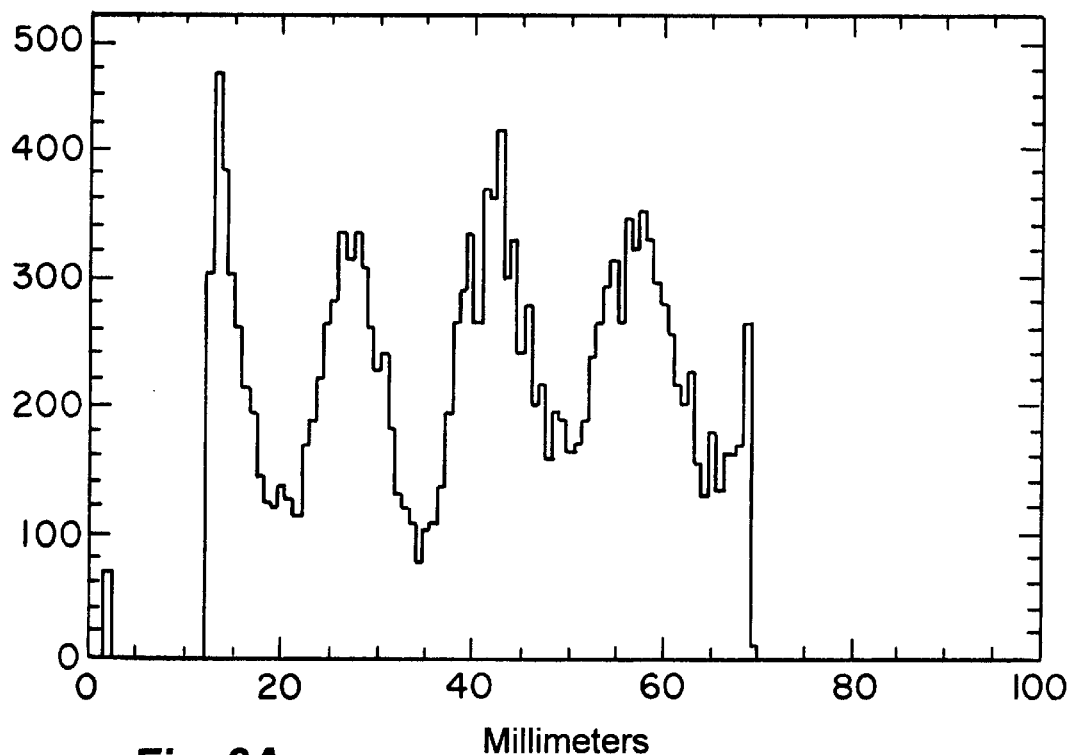
Fig. 8A  Millimeters
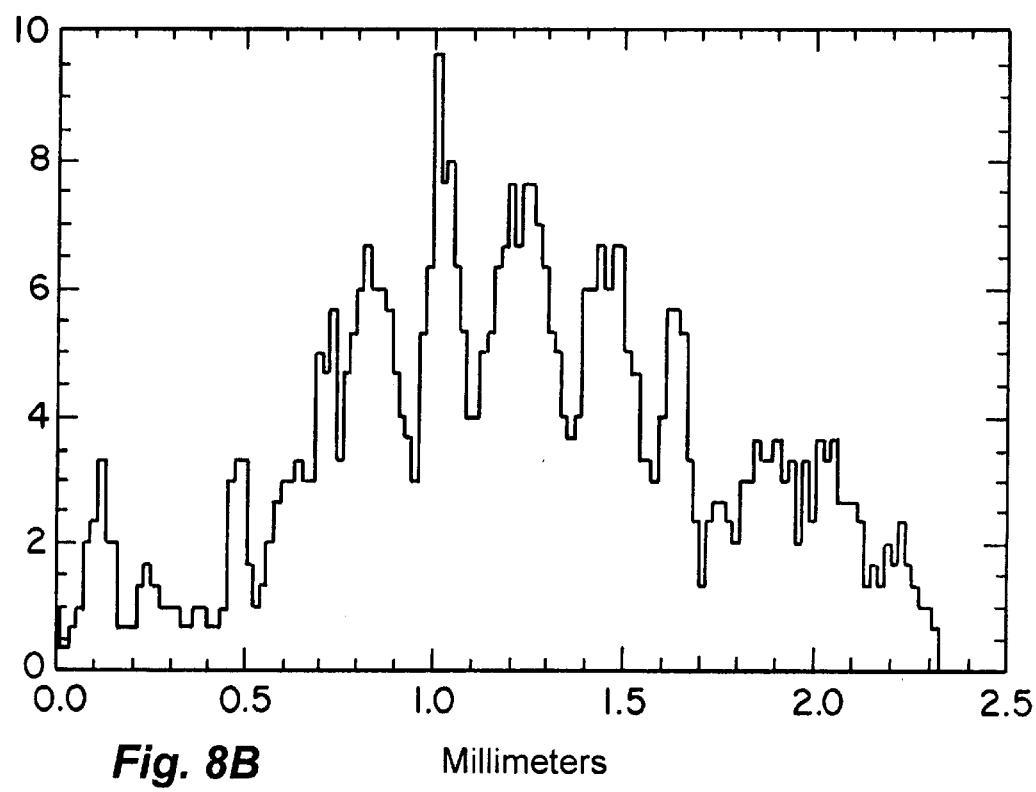
Fig. 8B  Millimeters

X-RAY INTERFEROMETER

RELATED APPLICATION

The present application is based on the Applicant's U.S. Provisional Patent Application Ser. No. 60/117,302, entitled "X-Ray Interferometer," filed on Jan. 26, 1999.

BACKGROUND OF THE INVENTION

1. Field of the Invention

The present invention relates generally to the field of x-ray optics and x-ray imaging. More specifically, the present invention discloses an x-ray interferometer for use in telescopes, microscopes and spectrometers.

2. Statement of the Problem

The creation of very high resolution x-ray optics is a formidable technical challenge, but one that holds promise of great scientific reward to the scientist. Such a device allows the astronomer to image x-ray sources in the sky with ultra-high resolution, the microscopist to study finer features, and both to perform sensitive spectroscopy of targets.

Even with optics of arbitrarily good performance, the effects of diffraction limit resolution. One way to achieve higher resolution is to exploit an approach that is widely used in the radio and optical spectral regions—interferometry. We show that a broadband x-ray interferometry is possible using current technology, and we have established the viability of this approach using laboratory measurements of a prototype interferometer.

For astronomers, interferometry has most frequently been used when imaging with resolution in excess of the diffraction limit is desired. A simple lens or mirror cannot image below $\theta = \lambda/D$, where $\theta$ is the resolution angle in radians, $\lambda$ is the wavelength, and D is the entrance aperture of the telescope. For example, a visible light telescope one meter in diameter cannot resolve features finer than one tenth of an arc second. At radio wavelengths, single dish telescopes can be built with diameters as great as a hundred meters, but the large wavelength still limits the resolution to a relatively poor 15 arc seconds.

Through maintenance of phase information, interferometry allows one to sidestep the problem of gigantism, and build functional, affordable systems. Two telescopes linked together interferometrically can resolve features as if they were a single telescope with a diameter equal to the separation. The intercontinental baselines encountered in radio interferometry support resolution of milli-arcseconds, without constructing a telescope thousands of kilometers in diameter.

X-ray interferometry provides two fundamental advantages for exploration of the universe. First, since the wavelengths are much shorter, the baselines can be greatly reduced. The resolution achieved using the intercontinental baselines used by radio astronomers can be matched by an x-ray baseline of only 10 cm. Second, many astronomical x-ray sources are hugely bright, allowing imaging of tiny structures that in other wavelength bands would emit too little signal to be seen at interstellar distances.

Microscopy is not usually linked to interferometry because, in the visible band of the spectrum, radiation can be bent through large angles with high precision. The diffraction limit of a microscope sets in at resolutions of $f\lambda$, where f is the focal ratio of the lens and $\lambda$ is the wavelength of the light. Since f/1 lenses can be fabricated for visible light, there is no need to break the radiation into separate channels. This is not true at x-ray wavelengths, where each reflection is at most a few degrees. Consequently interferometry has a role to play in x-ray microscopy.

To make an x-ray interferometer highly sensitive and generally useful, it must have certain properties:

(a) The instrument must be efficient, including not only high gathering power, but broad band pass.

(b) It should be adjustable. It is impractical to build a new device every time a different resolution or wavelength is desired.

(c) The interference fringes should be well behaved and predictable, so that inversion algorithms will function reliably.

(d) The fringe patterns should be well matched to high efficiency electronic detectors that are affordable and well behaved.

(e) The components should be readily available, i.e., the instrument should not require some critical component that requires heroic technical efforts to fabricate or maintain.

3. Discussion of Prior Art

X-ray interferometers have been made from Laue crystals since 1965 (Bonse et al., *App. Phys Lett*, vol. 6, p. 155 (1965)). These crystal interferometers have enjoyed substantial success in a limited range of applications. Because the diffraction of x-rays by crystals is efficient over only a small range of wavelengths, these systems tend to be inefficient, and are typically used in conjunction with very bright sources, like synchrotrons. Thus they have been used for microscopy, but have no potential for astronomy, where the sources are intrinsically fainter.

For high efficiency interferometry, we need a device that will operate over a broad band with good response. U.S. Pat. No. 4,174,478 (Frank) suggested the x-ray equivalent of a Michelson interferometer to split the amplitude of a beam using a thin metal foil. However, this still has limited band pass, operating only near the wavelength at which the beam is split equally between transmission and reflection. Additionally, a working model has never been demonstrated.

The alternative is to use reflecting optics to combine different parts of the wavefront, as opposed to splitting the wavefront. The optics can be crystals, multilayers, or grazing incidence mirrors. Both crystals and multilayers (which are often referred to as synthetic crystals) have narrow spectral response which can be useful, but tends to make the system inefficient. Grazing incidence, however, can have excellent reflectivity across a broad band.

The classic interferometers for visible light were described in the nineteenth century during the early development of the field. Of these, two in particular use wavefront division and are adaptable for use at grazing incidence (Born et al., *Principles of Optics*, 6th ed., Pergamon, New York, (1993)). The first is the Lloyd's mirror interferometer, in which the direct beam is interfered against a part of the wavefront that has reflected at grazing incidence off a flat mirror. The other is the Fresnel bent mirror interferometer, in which two flat mirrors reflect a single wavefront. A small angular offset between the reflected beams leads to interference fringes where the beams subsequently overlap.

Kellstrom used both a Lloyd's mirror geometry and a Fresnel bent mirror to create x-ray fringes (Kellstrom, *Nova Acta Soc. Sci. Upsala*, vol. 8, p. 60 (1932)). The Lloyd's geometry, while creating fringes and demonstrating the principle, is extremely inefficient in collecting area, requiring the mirror to operate at a vanishingly small graze angle (i.e. below one arc minute). The Fresnel option can be used at larger angles and is the closest to satisfying the needs of a practical system.

4. Solution to the Problem

None of the prior art shows an interferometer for use at x-ray wavelengths that meets all of the conditions for practicality in terms of speed, cost, complexity, size, throughput, and tolerances for an x-ray system. It is the lack of a system that exhibits all these properties that has made x-ray interferometry a difficult, expensive, time consuming proposition for the microscopist, and an impossibility for the astronomer.

The present application presents and demonstrates a concept for an interferometer that exhibits these crucially important properties. It can be built with existing optical components. It exhibits high efficiency across a large band of the spectrum. It is adaptable to the requirements of astronomy or other scientific disciplines. The concept is practical because it solves the twin problems of: (a) how to mix the beams without losing signal; and (b) how to feed the signal into the beam mixer in a way that will support multiple spatial and spectral frequencies.

The present application shows there is a highly practical means for mixing the x-ray beams without a beam splitter. The principle is somewhat similar to that employed in the classic Fresnel bent mirror geometry, but the present configuration is particularly adaptable to grazing incidence.

The idea is to create two diffraction limited wavefronts, and steer them together at a small angle, as shown in FIGS. 1 and 2. These figures show a plane wavefront from infinity impinging on two flat mirrors. These flats steer the beams onto a second pair of flats that re-direct the beams into quasi-parallel convergence.

The beam converger must cross the beams at the detector at a very low angle. This leads to large fringe amplification. The wavelength of the fringes on the detector is given by $\lambda L/d$, where d is the separation of the secondary mirrors at their centers and L is the distance from the centers of the mirrors to the detector where the beams cross. If L/d is large, the fringes can become macroscopic.

SUMMARY OF THE INVENTION

This invention provides an x-ray interferometer using at least one pair of reflectors at grazing incidence to create an interference pattern that is detected and subject to spectral analysis. By using two separate optical channels at grazing incidence to create interference from two areas of the wavefront, this system has broad band response and much higher efficiency. The interferometer has applications to telescopes, microscopes and spectrometers in the extreme ultraviolet and x-ray.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIGS. 8a and 8b are interference fringes recorded in the extreme ultraviolet and x-ray.

FIG. 8a shows the fringes for lines of argon at 920 Å.

FIG. 8b shows fringes recorded in the Mg Kα x-ray emission line at 1.25 keV.

DETAILED DESCRIPTION OF THE INVENTION

Figure 1:
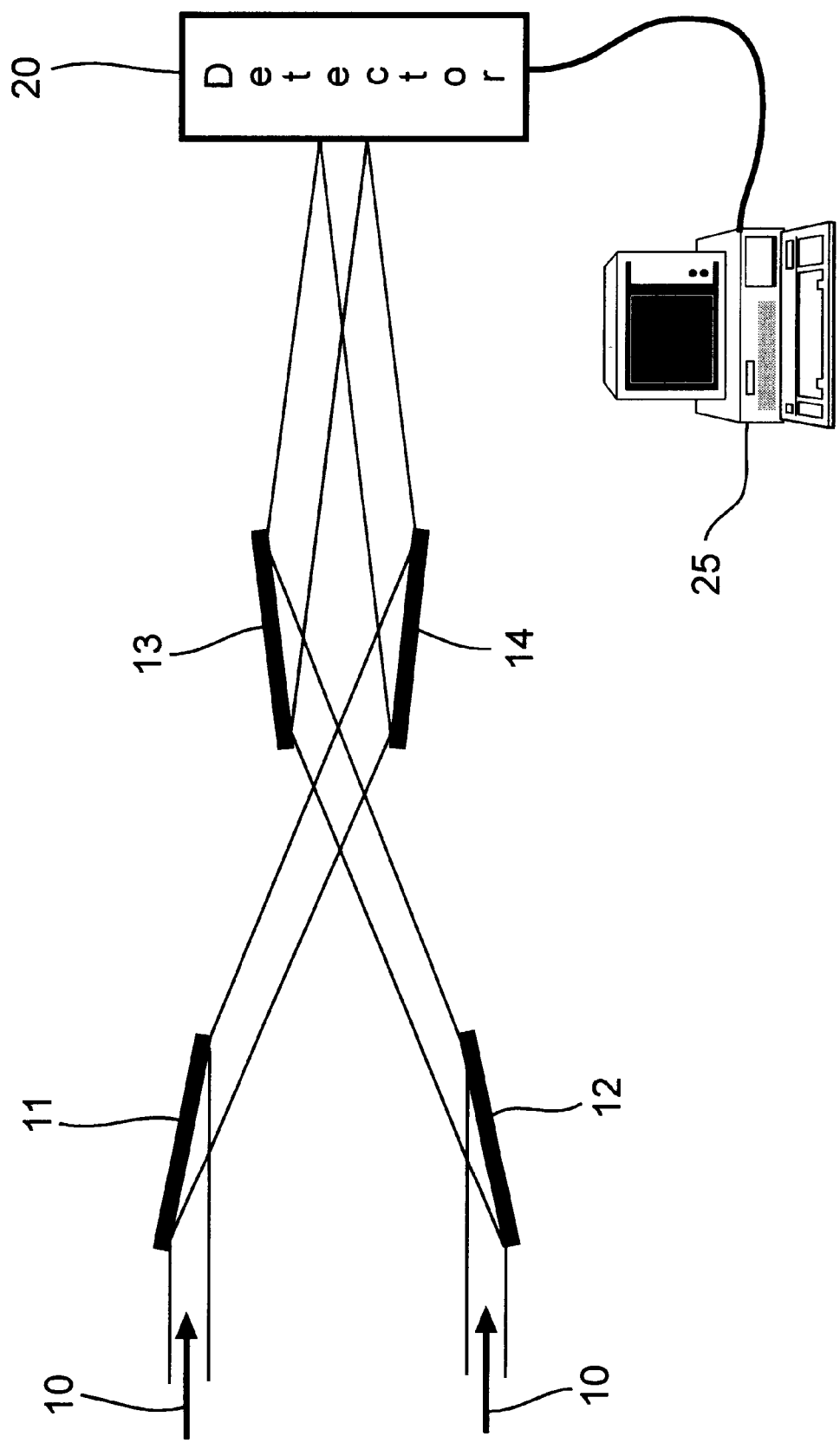
FIG. 1 is a diagram of the one arrangement of the mirrors at grazing incidence in the present invention.

FIG. 1 is a diagram of the one embodiment of the present invention. X-ray radiation from a distant source 10 strikes the pair of primary reflectors 11, 12 at grazing incidence and is reflected. The reflected x-ray beams converge, cross, and strike the secondary reflectors 13, 14 at grazing incidence. The reflectors 11–14 may be flats, but can be spherical or aspherical under some circumstances. For purposes of this disclosure, the terms "reflector" and "mirror" are used synonymously.

Figure 2:
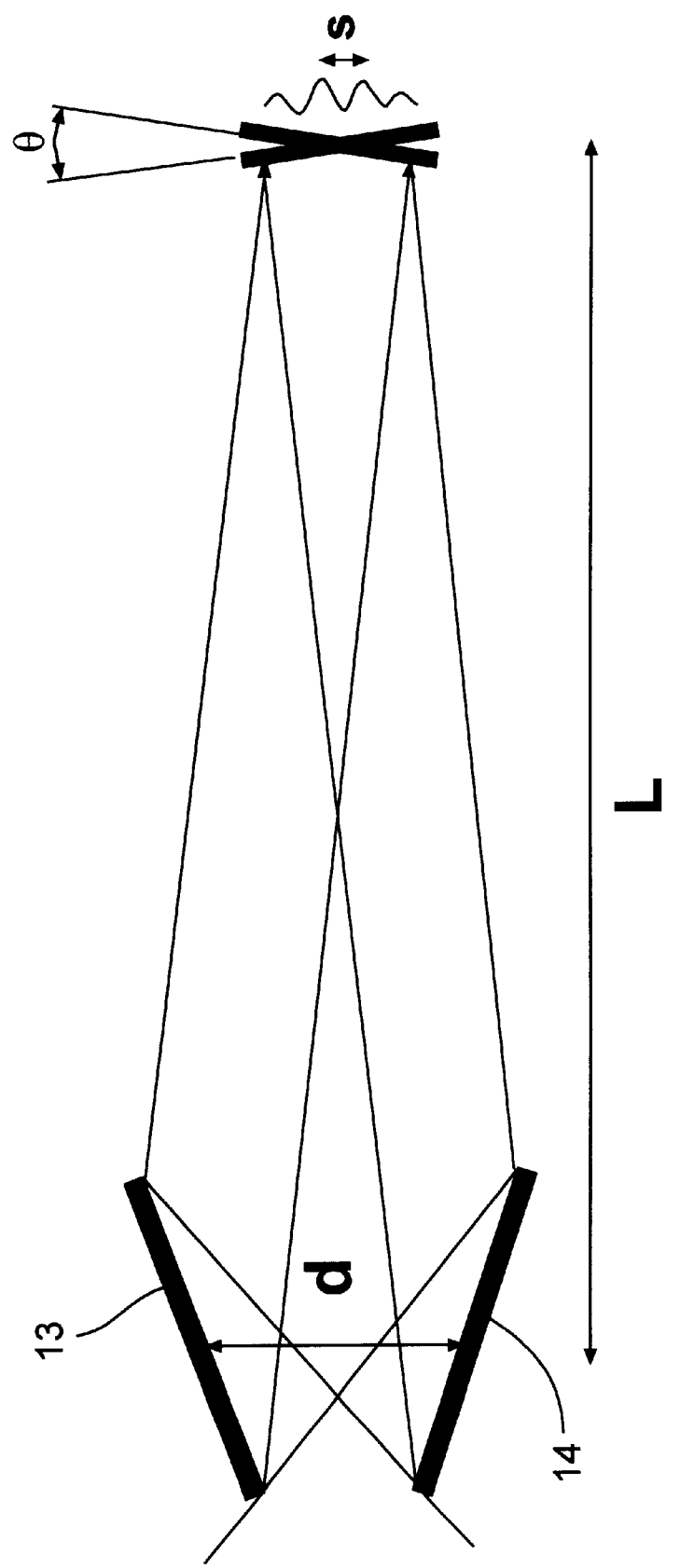
FIG. 2 is a detail diagram corresponding to the right portion of FIG. 1 showing the second pair of mirrors 13, 14 used to converge the beams to create an interference pattern at the detector 20.
Figure 4:
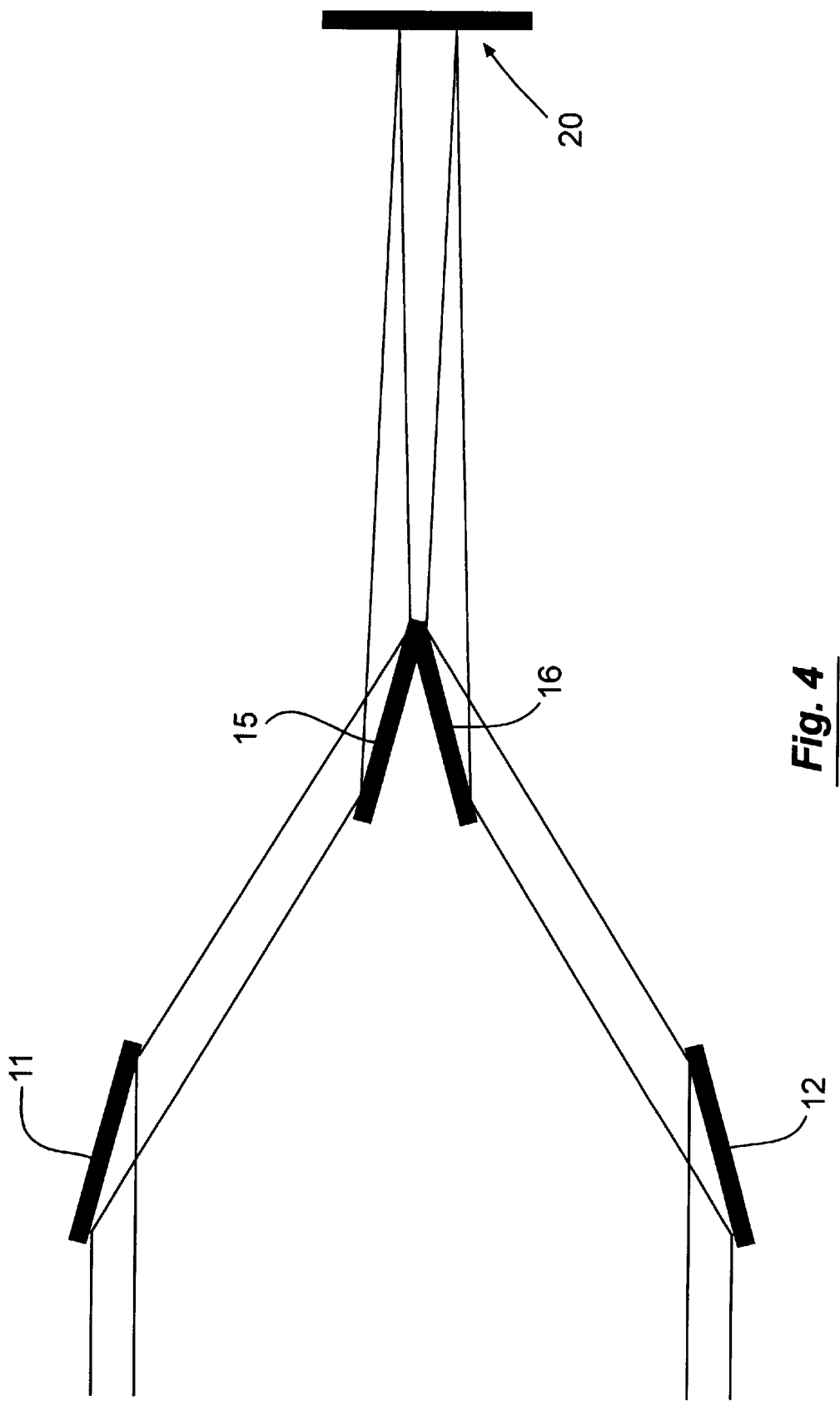
FIG. 4 is a diagram of an alternative arrangement of the mirrors in the present invention.

FIG. 2 is a detail diagram corresponding to the right portion of FIG. 1 showing the secondary reflectors 13, 14 used to converge the beams to create an interference pattern at the detector 20. This pair of reflectors 13, 14 acts as a converger that uses distance to mix the wavefronts at a low angle to produce an interference pattern at the detector 20. FIG. 4 is a diagram of an alternative arrangement of the secondary reflectors 15, 16. The detector 20 converts the interference pattern into electronic form so that it can be subject to spectral analysis by a computer processor 25, as will be described below.

For example, in the embodiment shown in FIG. 1, the secondary reflectors consist of first and second reflectors 13, 14 that reflect first and second beams of x-ray radiation at grazing incidence so that these beams intersect at a small angle to produce the interference pattern received by the detector 20. Optionally, a set of primary reflectors (i.e., a third reflector 12 and a fourth reflector 11 in FIG. 1) can be employed to reflect x-ray radiation at grazing incidence so that the reflected beams converge and are then reflected at grazing incidence by the secondary reflectors 13, 14.

X-ray interferometry is very challenging because of the very short wavelengths involved. Scattering and absorption properties of x-rays preclude the use of many of the standard techniques of visible light interferometry, and more stringent tolerances apply to the optical components that can be used at x-ray wavelengths. At first glance, the tolerances on the x-ray optics might seem to be impracticably severe. If the standard λ/10 figure of merit were imposed, the optics would have to have to be globally figured to sub-Angstrom accuracy. Fortunately, this is not necessary. At the grazing angles where x-ray optics reflect efficiently, the surface figure tolerances are relaxed significantly.

Figure 3:
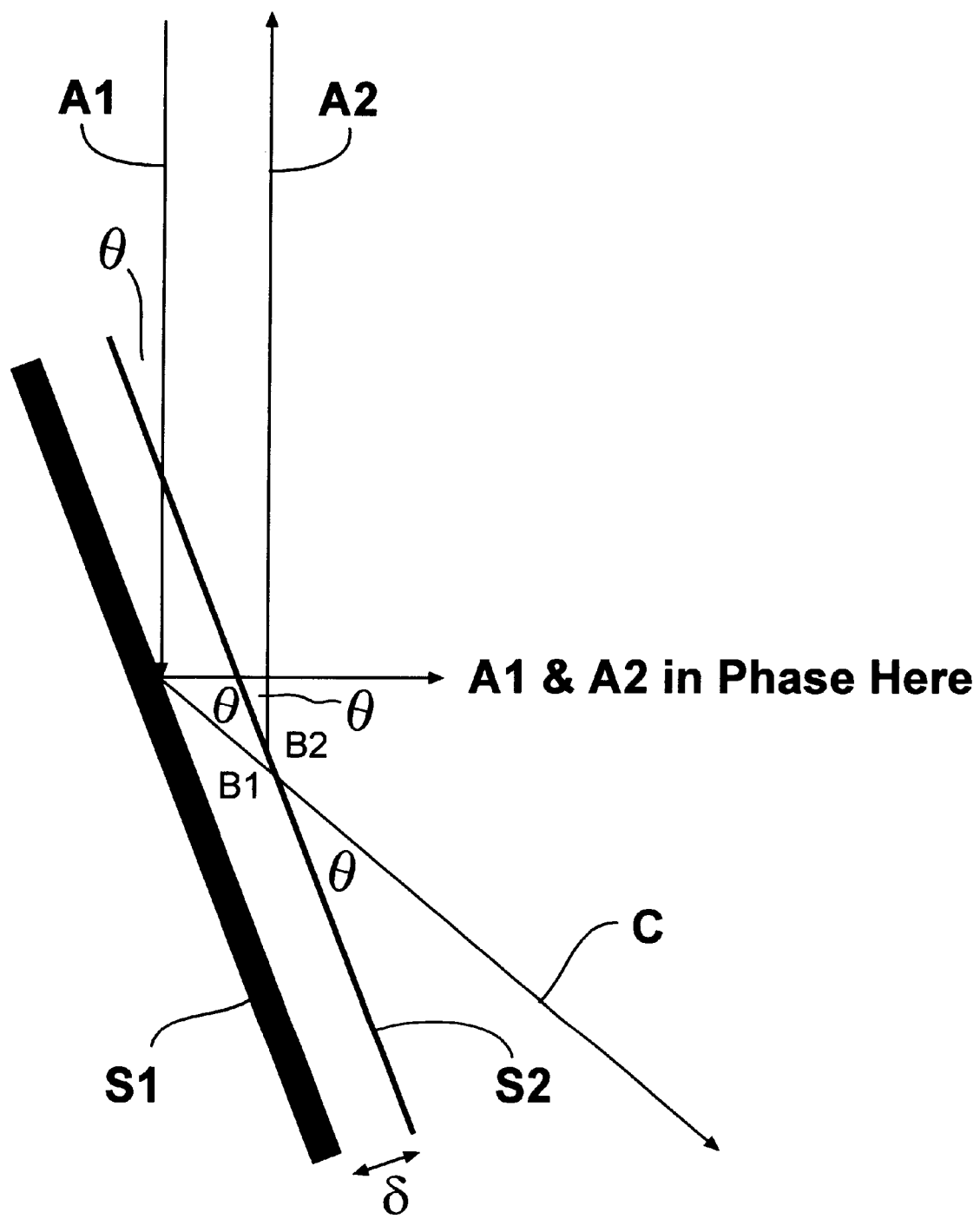
FIG. 3 is a diagram illustrating the tolerances of a grazing incidence interferometer. The rays A1 and A2 arrive in phase and both leave along ray C. The flat moves by δ to cause A2 to replace A1 along C. The result is a shift of phase at the focal plane. We find that δ can be no more than $\lambda_x/(20\sin\theta)$ if the fringe is to shift by less than a tenth of a period.

FIG. 3 is a diagram illustrating the tolerances of a grazing incidence interferometer. We look at a plane wavefront arriving at a grazing incidence mirror S1. We need to determine how much deviation is acceptable in the mirror. With no loss of generality, we analyze the case of a flat mirror which has moved a distance δ out of position in the direction normal to the surface. Assume that a plane wave arrives at the mirror. Initially the wave from A1 is reflected into the exit beam. When the mirror moves by δ the wave from A2 now exits along the same path toward the next optic or detector 20. It is straightforward to show that the change in path length (the optical path difference, or OPD) is given by δ(1-cos2θ)/sinθ. Application of the double angle trigonometric formula reduces this to a simple 2δsinθ.

Thus, if the phase emerging at a given point is not to change by more than $\lambda_x/10$, the surface must not move more than $\lambda_x/(20\sin\theta)$, where $\lambda_x$ is the wavelength of the x-ray and θ is the graze angle. The presence of the sinθ in the denominator is critical to the practicality of the system. To reflect 6 keV x-rays efficiently requires a 0.5 degree graze angle (sinθ≈0.01), leading to a full factor of one hundred reduction in the required stability of the optic. In fact, the grazing incidence optic can move five times the wavelength of the x-ray before the fringe shifts by one tenth. This means that the typical position tolerance is about 1.5 nanometers instead of 15 picometers—truly a big advantage.

The angular tolerance of each individual mirror can also be gleaned from FIG. 3. Consider that a rotation of α about the middle of the mirror causes a displacement of Lsinα/2 at the end. If Lsinα/2 is to be less than $\lambda_x/20\sin\theta$, then sinα must be less than $\lambda_x/10L\sin\theta$. Noticing that Lsinθ is the entrance aperture, and that $\lambda_x/L\sin\theta$ is the diffraction limit of the optic, then the rotation tolerance is simply one tenth of the diffraction limit. This makes perfect sense, as there is little information below the diffraction limit.

FIG. 3 provides information on the optical quality needed of the flat mirror. Any point on the mirror surface that deviates by more than $\lambda_x/20\sin\theta$ will create a component of reflected radiation that will be out of phase by more than a tenth of a wavelength. It is often acceptable to have some small percentage deviate by this much, so the actual specification should be given as a percentage of the surface area that can deviate more than this. If the specification is that the rms deviation is less than $\lambda_x/20\sin\theta$ then this translates to a 6.5 nm rms surface in the case of 1 nm x-rays and half degree graze angle. Fabrication of such optics is challenging, but lies within the state of the art.

Finally, it should be noted that the same tolerances apply to non-flat optics. With no loss of generality, the same diagram can be applied to a convex or concave optic. The same quantitative formulae apply. The same position and rotation tolerances apply without change. The needed quality of mirror remains the same, but it is substantially more difficult to figure and polish.

Creating Images. Creating images with an interferometer is one of the most important applications to the astronomer. Radio astronomers have been using interferometers to create images for decades. The problem has proven more difficult at shorter wavelengths, but true images are finally being acquired in the visible (e.g., Baldwin, et. al., *Astron. Astrophys.*, vol. 306, p. L13 (1996)). It now appears possible to consider the same goal in the extreme ultraviolet and x-ray.

A simple, two beam interferometer maps a point source of monochromatic radiation into an intensity sine wave. Thus a Fourier transform can recover the intensity and phase. With the acquisition of multiple frequencies, a full image can be reconstructed from the individual sine patterns.

The standard form for the analysis assumes an initial source intensity I(l,m) in two dimensions given by the variables l and m. The simple two aperture interferometer maps the output into a sine wave V(u, v), where u and v are the wave phases in two dimensions. V for a single source I at l,m can then be written:

$$V(u,v)=I(l,m)e^{-2\pi i(ul+vm)}$$

and when I(l,m) is a distribution of intensities over l and m (i.e., an image) we have:

$$V(u, v) = \int\int I(l, m)e^{-2\pi i(ul+vm)}dldm$$

This is the functional form of a Fourier transform and we can thus recover the intensity and phase by performing the transform:

$$I(l, m) = \int\int V(u, v)e^{2\pi i(ul+vm)}dudv$$

If V(u,v) can be measured at all values of u and v, then the integral can be evaluated directly, and the image reconstructed. In practice, the value of V at a finite number of values for u and v is recorded, and the integral is approximated. However, with the acquisition of a modest number of frequencies and rotation angles, a full image of good quality can be reconstructed.

In x-ray wavelengths, we have an advantage over visible light and radio interferometers. Our detector 20 can record individual photons and tag each with an energy. A simple CCD gives resolution as good as E/δE of 20, while quantum devices are approaching resolution of 1000. With no loss of signal, the data can be separated into separate sine waves of different frequencies. To the extent that the source does not change as a function of emission wavelength, this represents an improvement in our sampling of frequency space. It also allows us to record multiple fringes with little or no confusion.

Optimization of the algorithms may require significant work. While we can base our approach on that of the radio astronomers, our noise sources and systematic errors are entirely different.

Creating Spectra. The present interferometer can also give us information about the wavelength of the radiation incident. If the source is unresolved, then each wavelength produces a sine wave with frequency proportional to wavelength. The total signal received is the sum of these sine waves. We have created a Fourier transform spectrometer.

Possible Fourier transform spectrometers have been discussed in the literature, but these have assumed that the Fourier transform would be taken in the time domain (Howells et. al., *Nucl. Instrum. Methods A*, vol. 347, p. 182 (1994)). In our system, we get the information from the spatial domain which is exceptionally important, as x-ray sources are notoriously variable in time. Currently x-ray spectroscopy is accomplished by either diffractive means or by direct measurement of photon energy in a detector.

Concentrating the Beam. The biggest single disadvantage to using flat optics is the distance, L, required between the converger (i.e., secondary reflectors 13, 14 in FIG. 2) and the detector 20. To magnify the fringes from one wavelength (1 nm) to the 100μ detectable with CCD's requires a convergence angle of $10^{-5}$ radians. Thus, if the beams are 1 cm square, the distance from converger to detector must be on the order of 1 km. Such baselines are possible with today's technology and may well be the overall best way to accomplish some scientific goals.

However, it is possible to build the interferometer in a tighter space. The angle of convergence cannot be reduced, but the size of the beam can. If we used curved-surface optics to concentrate the beam without destroying the diffraction limited wavefront, then the image can be reduced in size and the detector brought closer to the converger. This of course requires that we build diffraction-limited optics that concentrate the radiation.

It is indeed possible (Gallagher et al., Proc. Soc. Photo-Opt. Eng., vol. 2805, p. 121 (1996)). Use of spherical mirrors in a Kirkpatrick-Baez mount can achieve the needed quality. Other approaches such as Wolter optics also work in theory but are difficult to build. The Chandra Observatory mirrors are probably within one order of magnitude of the needed quality, indicating that Wolters optics remain viable (Van Speybroeck et al., Proc. Soc. Photo-Opt. Eng., vol. 3113, p. 89 (1997)).

One side effect of the concentrator is that each mirror must remain fixed in its focal position. In the flat mirror system it is possible to physically change the separation of the flats, thereby changing the resolution of the system. This, of course, can be solved by using moveable flats to re-direct the wavefronts into the concentrating optics at the cost of extra complexity and signal loss.

Phased Arrays of Reflectors. A geometry that has particular appeal as a variation on the simple pair of flats is to place a phased array of reflectors around a common center. For example, the array of reflectors can be arranged in one or more concentric rings 51, 52 as shown schematically in FIG. 5. Here, a ring of primary reflectors 51 reflect x-ray radiation at grazing incidence to feed a ring of secondary reflectors 52, which also reflect the x-ray radiation at grazing incidence. The resulting beams from the secondary reflectors 52 mix at the detector. Each pair of opposing reflectors creates fringes. However, every pair of flats, even those not opposed interfere at a different frequency.

Figure 5:
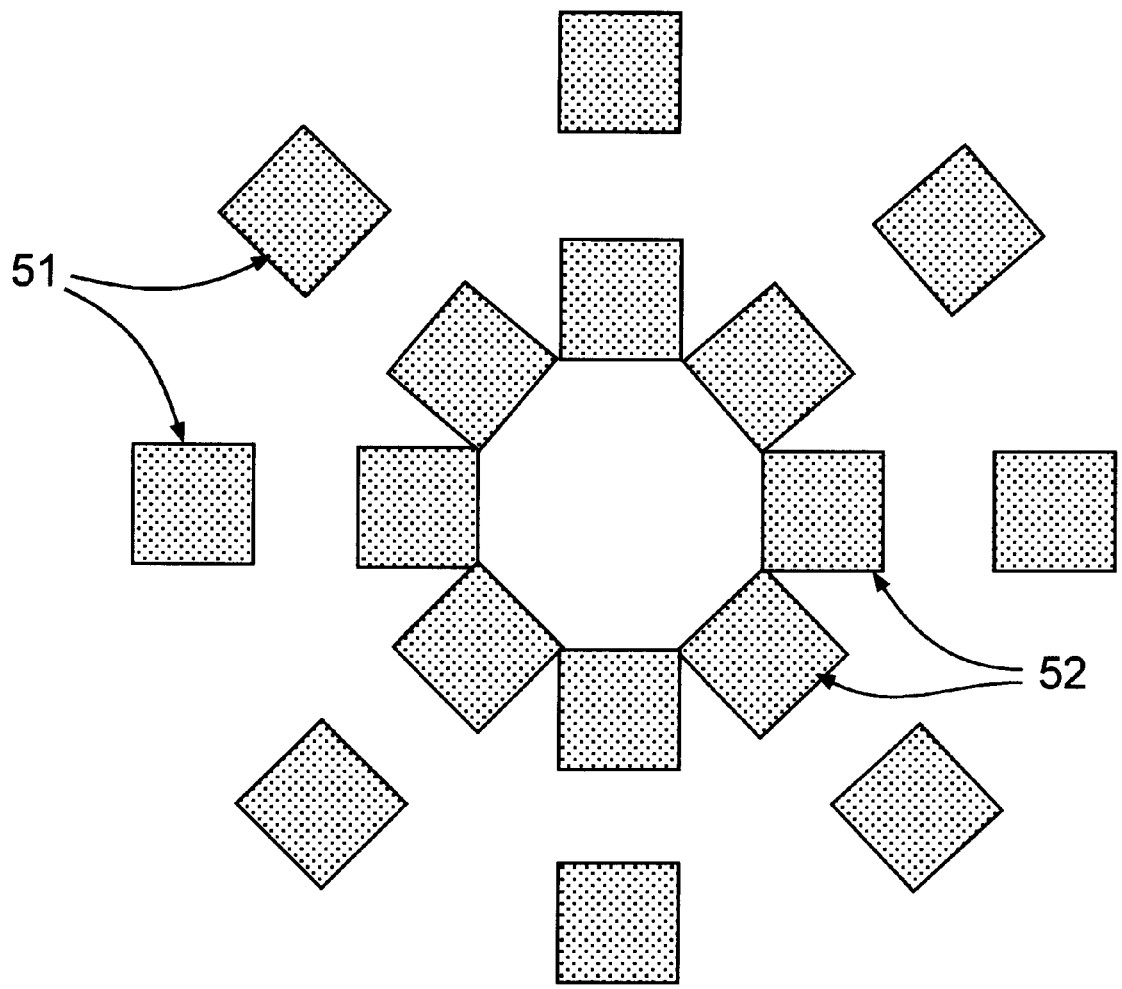
FIG. 5 is a schematic diagram showing a ring of primary mirrors 51 feeding a ring of secondary mirrors 52.

Other geometries could be used in place of the rings of reflectors 51, 52 shown in FIG. 5. For example, the reflectors can be arranged in a cross shape about a common center. Other radially symmetrical patterns could be used to create a phased array of reflectors.

We have simulated the effects of using multiple sets of reflectors held in phase, and the results are not only interesting, but artistic. FIGS. 6a through 6f are examples of the interference patterns produced by arrays of 2, 4, 8, 12, 16, and 32 mirrors, respectively. With one pair of reflectors, we see the familiar fringes in FIG. 6a. The addition of just two more mirrors changes the point response function to a square array of points in FIG. 6b. With eight or more mirrors, the point response function becomes a complex pattern of circular structures, as shown in FIGS. 6c through 6f. However, as the number of mirrors increases, the secondary peaks are driven farther away from an ever-brighter central point.

As the array of flats is moved, the imaged point moves around the field of view. This is exactly the same behavior a point source exhibits in the field of a telescope or microscope as the pointing changes. We can create direct images in this interferometer without recourse to image reconstruction in a computer. In some sense we are building a diffraction-limited optic out of a phased array of flats.

Figure 6A:
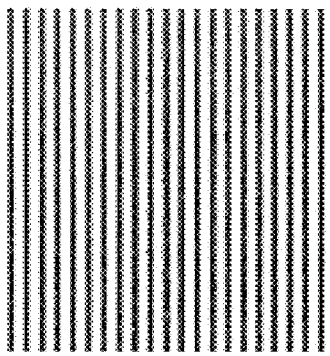
FIGS. 6a through 6f are examples of the interference patterns produced by arrays of 2, 4, 8, 12, 16, and 32 mirrors, respectively.
Figure 6B:
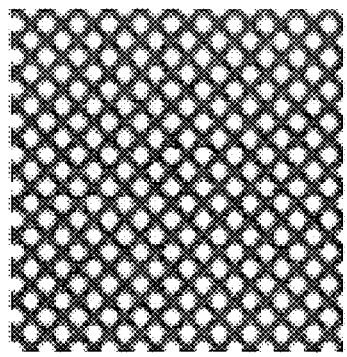
Figure 6C:
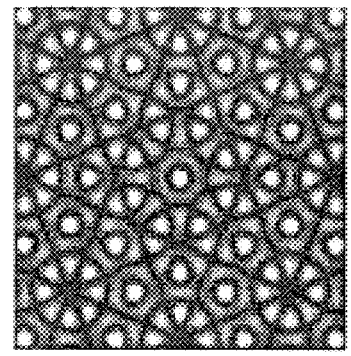
Figure 6D:
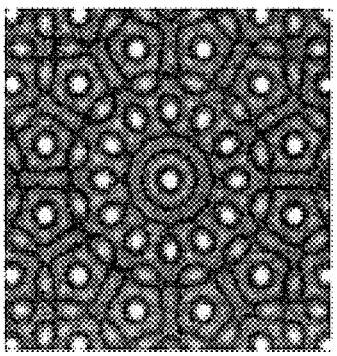
Figure 6E:
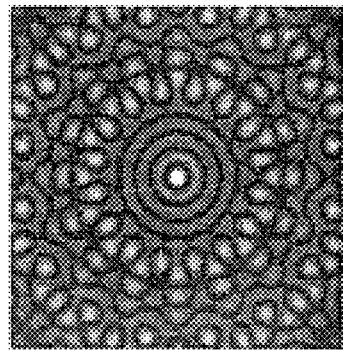
Figure 6F:
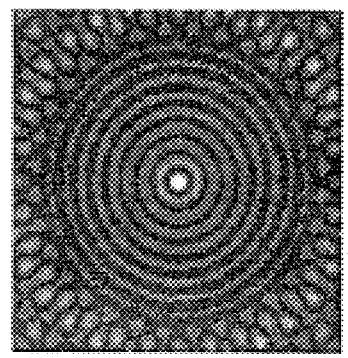

The diameter of the clear area around the central peak is roughly equal to the number of mirrors. That is, if 32 flats are used in the array (as shown in FIG. 6f), then the field of view will allow 32×32 diffraction limited spikes in the field. So, 32 mirrors set around the diameter of a one meter circle, operating at 1 nm (1.2 keV) will achieve a resolution of $10^{-9}$ radians (0.2 milli-arcseconds) in the central point, and a full image of a region 6.4 milli-arcseconds square will emerge on the detector. If the beam is wide enough, the image can extend farther from the center but will experience some confusion that will have to be removed by image manipulation.

This system has a huge advantage as it automatically multiplexes many different frequencies against each other, to suppress spurious peaks, and automatically create an image. The biggest disadvantage is that the individual mirrors must all be nulled so as to provide equal path length for the beam, and they must be held in null during the observation.

Figure 10:
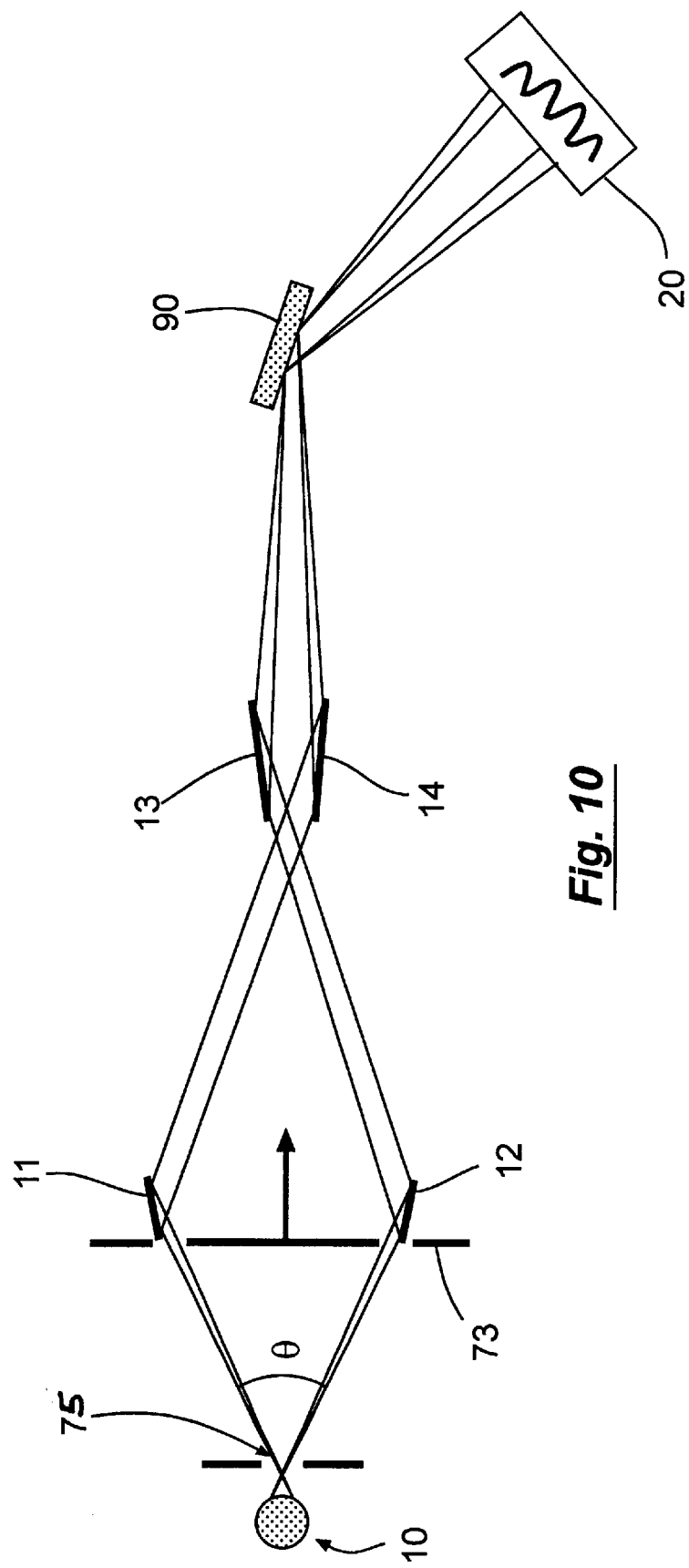
FIG. 10 is a diagram of the present invention configured as a microscope.

Microscope. FIG. 10 is a diagram of the present invention configured as a microscope. To obtain x-ray microscope images, the simplest adaptation is to rotate the instrument to sample different azimuths. A change in the separation of the primary mirror pair, and then another rotation will sample a different set of spatial frequencies across the target 75 held by a stage. With an adequate number of angles and separations, an image can be reconstructed. Of course, we can use the phased array configuration discussed earlier to minimize the number of separate observations needed.

The potential for high performance microscopy is good. The system samples an entire image at once, sidestepping the need to scan, and making better use of the radiation incident on the target 75. In a 100×100 resolution image, this is a 10,000 fold improvement in speed, allowing the use of conventional electron impact x-ray sources, avoiding the need to take the instrument to a powerful synchrotron. Since the detector can be used to identify the energy of each photon, it is not necessary to filter the signal by energy, also greatly enhancing the signal that can be used.

The resolution can be excellent. The limiting resolution of a microscope using interferometry is $f\lambda_x/2$, where f is the focal ratio of the beam. At 0.4 keV, in the "water window", graze angles are as high as 5 degrees. This implies that two mirrors can fold through a total angle of 20 degrees for a focal ratio of 3 and would limit the instrument resolution at about 6 nm. With the use of multilayer reflectors, f can approach unity and the resolution can approach 2 nm. At 6 keV, multilayers can support reflection at graze angles as high as 2 degrees, for an effective focal ratio of 7 and a resolution limit of 0.6 nm. A multiple reflection design could, potentially, get even finer.

An alternative approach is to demagnify the image of the slit interferometrically, by crossing the wavefronts from a distant slit at a large angle. (Polack et al., Rev. Sci. Instrum., vol. 66, p. 2180 (1995)). This creates microscopic fringes on a target. A ring of flats can create a spot-shaped micro-probe that can then be used in a scanning mode to build an image of the target.

High Contrast Imaging. A novel use of this class of interferometer is encountered when one considers putting visible light through the system instead of x-rays. The use of grazing incidence coupled with state-of-the-art mirrors, allows one to maintain phase to a fraction of an x-ray wavelength (i.e. a 100 pico-meters or better). The phase change of a visible light wavefront would also be held to 100 pico-meters or better. This is a very tiny fraction of the wavelength that is usually not detectable as it is well below the diffraction limit.

When more than two wavefronts are mixed to create fringes that interfere in a specific way, the small change in phase can become important. Multiple beams can be mixed at precise phases to create a null region, where light coming from one direction creates destructive interference and light from a different direction interferes constructively. This can allow the instrument to detect very faint sources close to very bright ones. High precision maintenance of the phases of the beams allows the destructive interference to be precisely maintained, and very little of the light from the other source can scatter into the null region.

The most obvious application of such a system is astronomical in nature. Astronomers wish to first detect, and then image the planets in orbit around nearby stars. However, an Earth-like planet can be one billion times fainter than the star that illuminates it, yet is less than one arcsecond away. The amount of scatter, S, in an interferometrically created null scales as:

$$S \propto \left(\frac{\sigma \sin\theta}{\lambda}\right)^2$$

where $\sigma$ is the size of the deviations, $\lambda$ is the wavelength of the radiation and $\theta$ is the graze angle. The best available mirrors have $\sigma/\lambda$ of about 0.01, so scatter tends to ruin the null at the level of $10^{-4}$. With the addition of the $\sin\theta=0.01$ term at grazing incidence, the null can be improved down to the $10^{-8}$ level.

Figure 7:
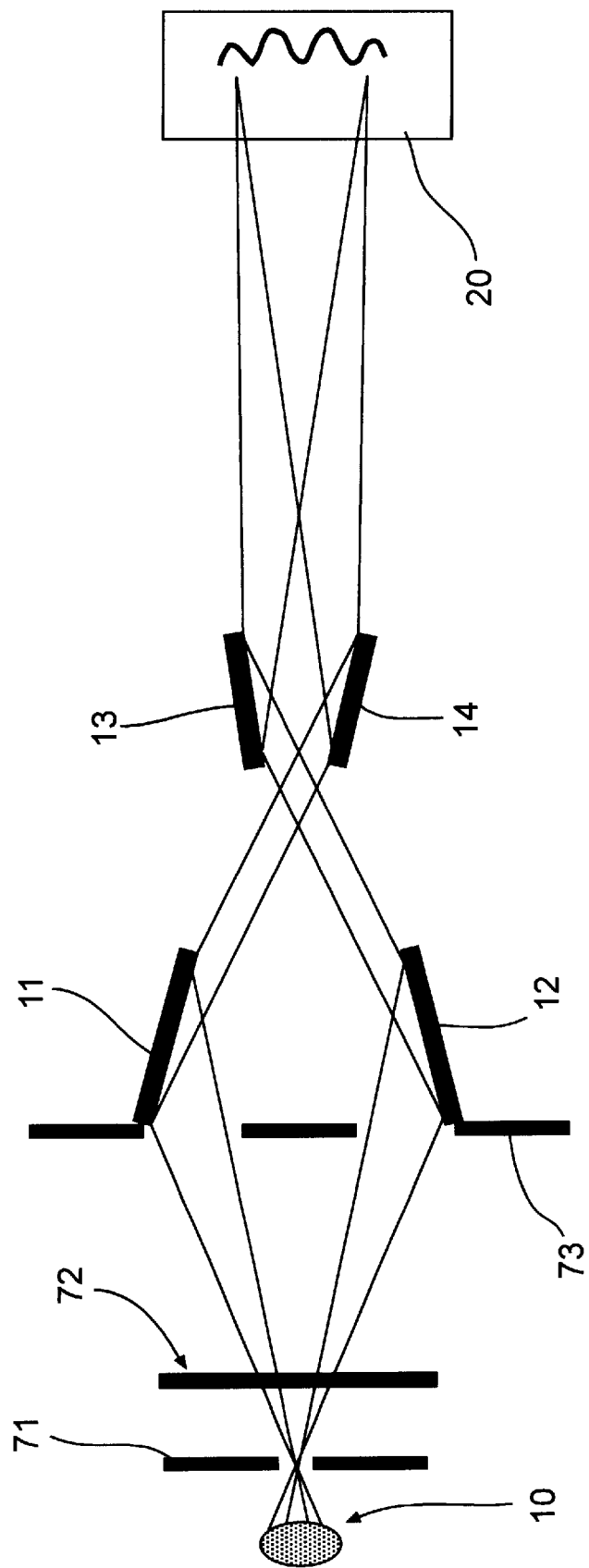
FIG. 7 is a diagram of an interferometer used to create x-ray fringes in the laboratory from an x-ray source 10.

Example. An essential step in establishing the viability of the interferometer is the demonstration of a practical x-ray interferometer. We have now built and successfully tested an interferometer of this class at extreme ultraviolet (EUV) and x-ray wavelengths. FIG. 7 is a diagram of an interferometer used to create x-ray fringes in the laboratory from an x-ray source 10. In this section we describe the experiment and show some results.

The instrument used the four flat mirror design shown schematically in FIG. 7. Tests were performed in a 120 meter long vacuum facility at the Marshall Space Flight Center. Photons were generated in compact sources of x-ray and EUV radiation. The system is sufficiently sensitive that super bright sources like synchrotrons are not needed. In each case the source was mounted behind an entrance slit 71. Sixteen meters from the slit 71, the divergent beam entered the interferometer. An entrance aperture that consisted of two parallel slits 73 ensured that the two primary mirrors 11, 12 were illuminated, but that none of the direct beam could enter the interferometer without reflecting off the optics. After passing the double slit 73, the wavefronts reflected on the primary reflectors 11, 12. Each reflector was a 50 mm circular optical flat set at 0.25 degrees to the incoming beam. Each was mounted in a precision manipulator that allowed fine rotational and translation adjustment from outside the vacuum tank. The front edges of the primary reflectors 11, 12 were separated by 0.76 mm and the back edges by 0.55 mm. The primary mirrors 11, 12 created reflected wavefronts that crossed and were then reflected by the secondary mirrors 13, 14.

The fronts of the secondary mirrors were 16.97 mm beyond the back of the primaries. These mirrors were also 50 mm diameter circular optical flats mounted on manipulators. They were set 0.40 mm apart at the front, and 0.61 mm apart at the back. The wavefronts, when they emerged from the secondary mirrors 13, 14, were very nearly parallel. They then traveled 100 meters down the vacuum pipe to the detector 20.

In July, 1999, we used the facility at Marshall Space Flight Center to investigate performance in the extreme ultraviolet. For this wavelength range we used a microchannel plate detector (Gallagher et al., *Proc. Soc. Photo-Opt. Eng.*, vol. 2805, p. 121 (1996)). The photon source 10 was a hollow cathode discharge source (Van Speybroeck et al., *Proc. Soc. Photo-Opt. Eng.*, vol. 3115, p. 89 (1997)) that creates very bright emission lines from noble gases. We used $0.15\mu$ thick aluminum filter 72 to isolate the EUV portion of the spectrum and a $200\mu$ wide entrance slit 71.

FIGS. 8a and 8b show some of the results. In particular, FIGS. 8a and 8b are interference fringes recorded in the extreme ultraviolet and x-ray, respectively. FIG. 8a shows the fringes for lines of argon at 920 Å. The signal was bright, and the size of the fringes was large since the whole system had been optimized for smaller wavelength x-rays. In FIG. 8a, we show a profile of the fringes generated when argon was used in the source. The emission was from Lyman $\alpha$ line of neutral and singly ionized argon (ArI 1048, 1067 Å, and ArII 920, 932 Å). The fringes are broad and clear. The central fringe is a little higher, indicating that the emission lines were not pure, and other wavelengths were reaching the detector. It is only in the central fringe that all wavelengths are in phase. Thus the central fringe is identifiable by its extra height.

We performed the experiment of placing a block across the entrance to one of the two channels of the interferometer. We found that the signal dropped a factor of two, and that the fringes disappeared as expected, confirming that we were, in fact, seeing interference from the wavefront division into the two channels of the interferometer.

For demonstration of the interferometer in the x-ray we used a Manson Model 5 electron impact source with a magnesium target and 2 micron aluminum filter to create a beam that consists mostly of the Mg K line (1.25 keV). The beam passed through a 5 micron exit slit. The x-ray imaging detector was a Loral CCD, with 18 micron pixels. The CCD was mounted in an Infrared Laboratories LN2-cooled cryostat which regulated the temperature of the CCD at about $-80°$ C. to suppress thermal dark current noise. The CCD system is interfaced via an Sbus controller to a Sun Sparcstation 5 for instrument control and data acquisition.

When the system was turned on, each of the two beams created a vertical stripe of illumination on the CCD about a millimeter wide. The final step was to fine adjust the angles of the secondary mirrors so that the two stripes fell on top of each other at the CCD. After adjusting the alignment by a few arcseconds we recorded the image in FIG. 8b. Within the stripe of illumination are the fringes we were seeking.

The photons in the image were rotated about half a degree to allow for the fact that the fringes were somewhat off vertical. The counts were then gathered into a histogram of events across the horizontal direction. A two bin boxcar smooth has been run across the data to suppress the Poisson noise.

The overall appearance of the fringes is similar to those accumulated in the extreme ultraviolet. The main difference is that they are much narrower on the focal plane, as is to be expected from the lower diffraction effects of the shorter wavelengths.

In this laboratory demonstration of fringes, we are already measuring microscopic information. For example, when a $10\mu$ slit 71 was used instead of $5\mu$, the fringes are significantly degraded. Thus we have already demonstrated some sensitivity to image microscopic image quality at the $10\mu$ level, even though the slit 71 was 16 meters from the interferometer. Had we been closer, the interferometer would have been sensitive to even smaller features.

Figure 9:
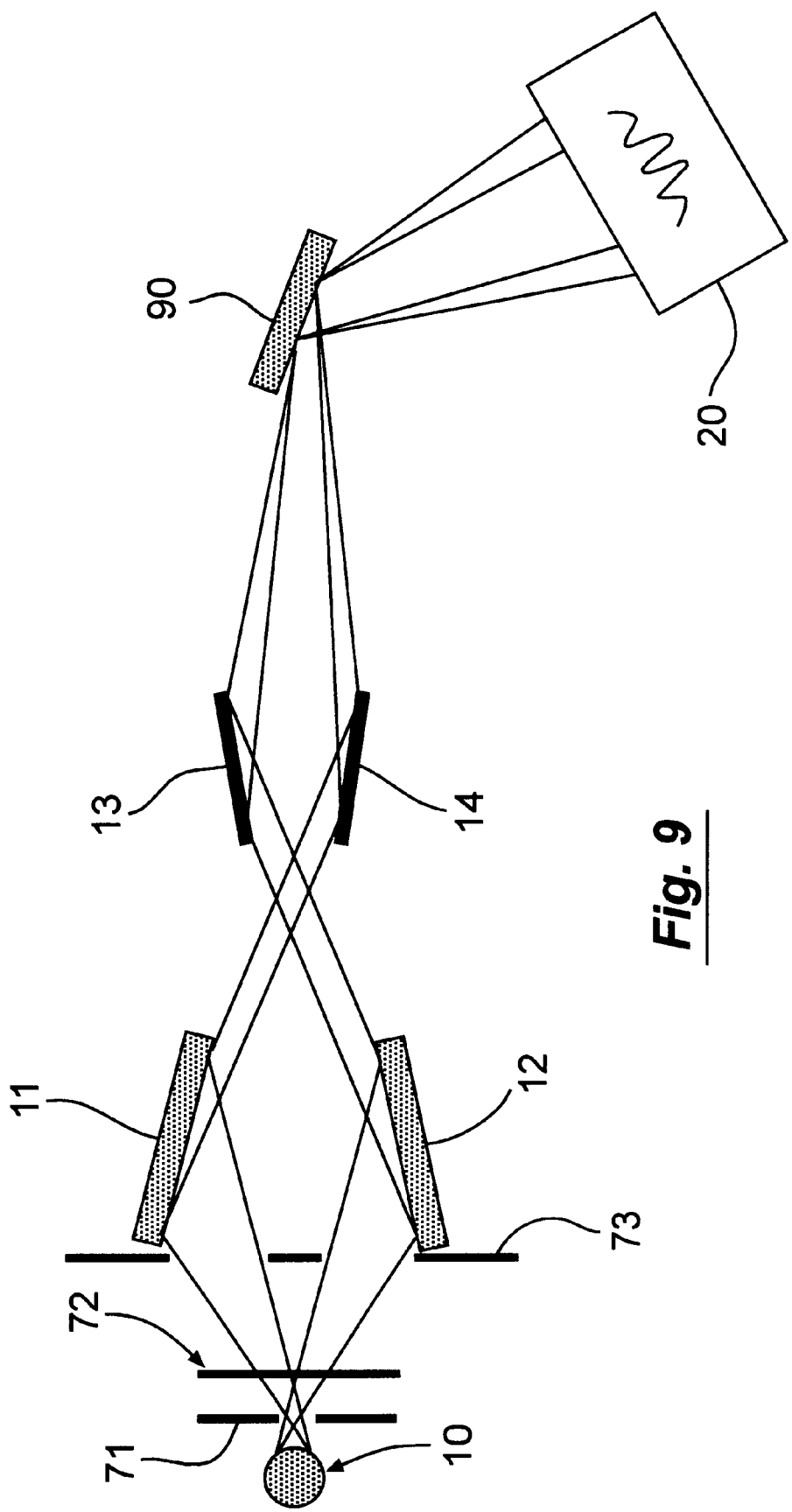
FIG. 9 is a diagram of an alternative embodiment of the interferometer in FIG. 7 with a spherical mirror 90 to magnify the interference fringe.

FIG. 9 is a diagram of an alternative embodiment of the interferometer in FIG. 7 with a spherical mirror 90 to magnify the interference fringe. This approach can also be applied to the microscope embodiment illustrated in FIG. 10.

The above disclosure sets forth a number of embodiments of the present invention. Other arrangements or embodiments, not precisely set forth, could be practiced under the teachings of the present invention and as set forth in the following claims.

I claim:

1. An x-ray interferometer comprising:

a first reflector reflecting a first beam of x-ray radiation at grazing incidence from an x-ray source;

a second reflector reflecting a second beam of x-ray radiation at grazing incidence from the x-ray source so that said first beam and said second beam intersect at a small angle to produce an interference pattern;

a detector receiving said interference pattern; and a processor for spectral analysis of said interference pattern from said detector.

2. The x-ray interferometer of claim 1 wherein x-ray radiation from the x-ray source passes through a target before being reflected by said first and second reflectors.

3. The x-ray interferometer of claim 1 wherein the x-ray source comprises an astronomical object.

4. The x-ray interferometer of claim 1 further comprising:

a third reflector reflecting a first beam of x-ray radiation at grazing incidence from an x-ray source onto said first reflector, so that said first beam is reflected at grazing incidence by said first reflector; and a fourth reflector reflecting a second beam of x-ray radiation at grazing incidence from the x-ray source onto said second reflector, so that said second beam is reflected at grazing incidence by said second reflector.

5. The x-ray interferometer of claim 1 wherein said first and second reflectors have substantially flat reflective surfaces.

6. The x-ray interferometer of claim 1 wherein said first and second reflectors have spherical reflective surfaces.

7. The x-ray interferometer of claim 1 wherein said first and second reflectors have aspherical reflective surfaces.

8. The x-ray interferometer of claim 1 further comprising a spherical reflector reflecting said first beam and said second beam to produce a magnified interference pattern.

9. An x-ray interferometer comprising:

a phased array of primary reflectors, each primary reflector reflecting a beam of x-ray radiation at grazing incidence from an x-ray source;

a phased array of secondary reflectors, each secondary reflector receiving and reflecting a beam from said primary reflectors at grazing incidence, so that said beams reflected by said secondary reflector intersect at a small angle to produce an interference pattern;

a detector receiving said interference pattern; and a processor for spectral analysis of said interference pattern from said detector.

10. The x-ray interferometer of claim 9 wherein said primary and secondary reflectors have substantially flat reflective surfaces.

11. The x-ray interferometer of claim 9 said primary and secondary reflectors have aspherical reflective surfaces.

12. The x-ray interferometer of claim 9 further comprising a spherical reflector reflecting said beams reflected by said secondary reflectors to produce a magnified interference pattern.

13. The x-ray interferometer of claim 9 wherein said primary reflectors are arranged as opposing pairs of reflectors.

14. The x-ray interferometer of claim 9 wherein said secondary reflectors are arranged as opposing pairs of reflectors.

15. An x-ray microscope comprising:

an x-ray source;

a stage for positioning a target relative to said x-ray source;

a first reflector reflecting a first beam of x-ray radiation passing through the target from said x-ray source at grazing incidence;

a second reflector reflecting a second beam of x-ray radiation passing through the target from said x-ray source at grazing incidence, so that said first beam and said second beam intersect at a small angle to produce an interference pattern;

a detector receiving said interference pattern; and a processor for spectral analysis of said interference pattern from said detector.

16. The x-ray microscope of claim 15 further comprising:

a third reflector reflecting said first beam of x-ray radiation at grazing incidence from an x-ray source onto said first reflector, so that said first beam is reflected at grazing incidence by said first reflector; and a fourth reflector reflecting said second beam of x-ray radiation at grazing incidence from the x-ray source onto said second reflector, so that said second beam is reflected at grazing incidence by said second reflector.

17. The x-ray microscope of claim 15 wherein said first and second reflectors have substantially flat reflective surfaces.

18. The x-ray microscope of claim 15 further comprising a spherical reflector reflecting said first beam and said second beam to produce a magnified interference pattern.

* * * * *